United States Patent [19]

Amundsen et al.

[11] Patent Number: 4,921,847

[45] Date of Patent: May 1, 1990

[54] TRIHALO(AMINE)GOLD(III) ANTI-TUMOR COMPLEXES

[75] Inventors: Alan R. Amundsen, Somerville; Eric W. Stern, Mountainside, both of N.J.

[73] Assignee: Engelhard Corporation, Edison, N.J.

[21] Appl. No.: 316,555

[22] Filed: Feb. 27, 1989

Related U.S. Application Data

[63] Continuation of Ser. No. 198,656, May 23, 1988, abandoned, which is a continuation of Ser. No. 726,453, Apr. 24, 1985, abandoned, which is a continuation of Ser. No. 392,820, Jun. 28, 1982, abandoned.

[51] Int. Cl.$^5$ .................... A61K 31/21; C07F 1/12
[52] U.S. Cl. .................... 514/188; 544/225; 546/2; 548/101; 556/110
[58] Field of Search ................ 546/2; 514/188

[56] References Cited

U.S. PATENT DOCUMENTS

| | | | |
|---|---|---|---|
| 4,171,360 | 10/1979 | Hill | 546/2 |
| 4,201,719 | 5/1980 | Liang | 548/101 |
| 4,243,663 | 1/1981 | Azuma et al. | 424/181 |
| 4,267,172 | 5/1981 | Toyoshima | 424/184 |
| 4,325,946 | 4/1982 | Bargiotti | 424/181 |
| 4,375,464 | 3/1983 | Schgalita | 424/122 |
| 4,427,657 | 1/1984 | Toyoshima | 424/177 |

FOREIGN PATENT DOCUMENTS 2528851 12/1983 France.
841855 9/1955 United Kingdom.
2122194 1/1984 United Kingdom.

OTHER PUBLICATIONS

Zelenov Chem Abs 76, 92637h (1972).
Krakovyak, et al. Chem abs 70, 20467(f).
Chemical Abstracts–V. A. Belonosov et al. "Synthesis and study of complexes of gold (III) with 3(5)-methyl--and 3,5-dimethylpyrazoles" vol. 94, No. 26, Jun. 29, 1981, p. 710.
Chemical Abstracts–A. Shamin et al. "Novel alkylpyrazine complexes of less common netals–II" vol. 103, No. 4, Jul. 29, 1985, p. 605.
Chemical Abstracts–A. L. Bandini et al. "Some gold-(III) derivatives of pyrazoles" vol. 103, No. 6, Aug. 12, 1985, p. 684.

*Primary Examiner*—Mark L. Berch

[57] ABSTRACT

There is described a novel class of aminegold(III) complexes in which the nitrogen-containing ligand is an alkylamine, an arylamine or a heterocyclic amine. Said complexes are useful in the treatment of tumors in mammals.

13 Claims, No Drawings

TRIHALO(AMINE)GOLD(III) ANTI-TUMOR COMPLEXES

This is a continuation of copending application Ser. No. 198,656 filed on May 23, 1988 which is a continuation of Ser. No. 726,453 filed Apr. 24, 1985, which is a continuation of Ser. No. 392,820 filed June 28, 1982 all now abandoned. This invention relates to gold (III) complexes comprised of a nitrogen containing ligand and chloride or bromide. This invention also relates to pharmaceutical compositions which contain one or more of said complexes as an active ingredient and to a method for the treatment of tumors via the administration of same.

Aminegold complexes are disclosed in the literature but none of these have proven to be clinically useful in the treatment of tumors; therefore, this invention constitutes an advance in the art because it adds to the known family of anti-tumor agents a new and rationally developed class of aminegold(III) complexes.

The discovery that Cisplatin is effective against human cancers aroused interest initially in precious metal complexes as a source of anti-tumor agents. Although many new platinum compounds have been shown to be useful in the treatment of tumors and although some gold complexes are used in the treatment of arthritis, (D. H. Brown, et al; Chemical Society Reviews, Vol. 9: page 217–240 (1980)) there is no evidence in the literature to suggest that trihalo(amine)gold(III) complexes can be used as anti-tumor agents.

Accordingly, there is a need for gold complexes which exhibit anti-tumor activity and which can be administered orally or parenterally.

THE INVENTION

This invention relates to a novel class of trihalo(amine)gold(III) complexes which are useful as anti-tumor agents in mammals. These compounds exhibit excellent activity against malignant tumor cells in animals as well as low mammalian toxicity.

It is a further object of this invention to provide gold complexes which may be administered both orally and parenterally.

In its broadest aspects, this invention relates to gold complexes having the formula: $AuLX_3$ where Au represents gold, L is a nitrogen-containing ligand such as an aliphatic amine, an aromatic amine or a heterocyclic amine and X is chloride or More specifically, this invention relates to compounds of the formula:

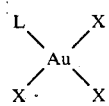

wherein:

Au represents gold in its trivalent state, i.e., Au(III);
L is a member selected from the group consisting of a pyridine of the formula:

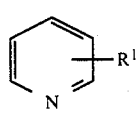

wherein $R^1$ is selected from among: $C_{1-6}$ alkyl as, for example, methyl, ethyl, n-propyl and the like; carboxy; $C_{2-6}$ alkanoyl as, for example, acetyl, n-propionyl or n-butyryl and the like; $-C_nH_{2n}$ CooH wherein n is 1 to 6 as, for example, carboxymethyl or carboxyethyl and the like;

carbinol;

hydroxy; and $C_{1-6}$ alkoxy as, for example, methoxy, ethoxy, or n-propoxy and the like;

a pyridazine of the formula:

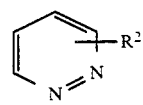

wherein $R^2$ is selected from among:

hydrogen and the same groups as $R^1$; a pyrimidine of the formula:

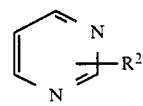

a pyrazine of the formula:

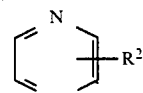

an imidazole of the formula:

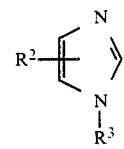

wherein:

$R^3$ is $C_{1-6}$ alkyl as, for example, methyl, ethyl and the like;

a pyrazole of the formula:

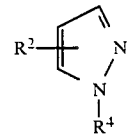

wherein;

$R^4$ is hydrogen or $C_{1-6}$ alkyl as, for example, methyl, ethyl, and the like; and alkylamine as, for example, an alkylamine of from about 1–6 carbon atoms but, preferably, a lower alkylamine of from about 1–3 carbon atoms such as methylamine, ethylamine, isopropylamine and the like;

an arylamine of the formula:

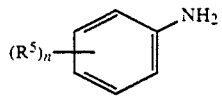

wherein $R^5$ is $C_{1-6}$ alkyl, $C_{1-6}$ alkoxy, hydroxy, $C_{2-6}$ alkanoyl, or halo such as chloro, bromo, or fluoro and the like and n is an integer having a value of 0-3; and X is selected from the group consisting of chloro or bromo with the proviso that X represents chloro when L represents 3-pyridylacetic acid.

The "proviso" in the definition of "X" excludes a species which is inactive as an anti-tumor agent under the test conditions hereinafter described. This species is the product formed when X represents bromo and L represents 3-pyridylacetic acid, that is, the tribromo(3-pyridylacetic acid)gold(III) of Example 10. See in this regard the % ILS data for this compound in Table 1, infra. By contrast, the complex which results when X is chloro and L is 3-pyridylacetic acid [i.e., trichloro(3-pyridyacetic acid)gold(III)]exhibits pronounced antitumor effect.

The compound wherein L is pyridine ($R_1$ is hydrogen) is referred to in the literature but no utility is suggested. It is useful herein to produce active pharmaceutical compositions.

A preferred embodiment of this invention relates to gold(III) complexes in which the nitrogen containing ligand is a mono substituted pyridine or imidazole of the formula:

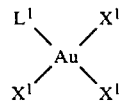

wherein $L^1$ is a member selected from the group consisting of a pyridine of the formula:

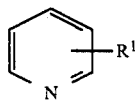

wherein $R^1$ is selected from among carboxy, $C_{2-6}$ alkanoyl, $-C_nH_{2n}$ COOH wherein n is 1 to 6 carbinol, hydroxy and $C_{1-6}$ alkoxy; and an imidazole of the formula:

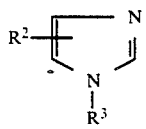

wherein $R^2$ is hydrogen and $R^3$ is $C_{1-4}$ alkyl; and $X^1$ is selected from the group consisting of chloro or bromo, with the proviso that $X^1$ represents chloro when $L^1$ represents 3-pyridylacetic acid.

This class of complexes exhibits a pronounced anti-tumor activity in mammals and it is useful in oral and parenteral administrations over a wide range of dosages.

An especially preferred subgroup within this embodiment consists of $Au(III)L^1(X^1)_3$ complexes in which $L^1$ represents a ligand selected from the group consisting of (1) a pyridine substituted by carboxy or $C_{2-6}$ alkanoyl, or (2) an N-$C_{1-4}$ alkyl imidazole; and $X^1$ is chloro or bromo. Typical of the nitrogen-containing ligands ($L^1$) falling with this subgroup are, for example, nicotinic acid, 3-acetylpyridine and N-methylimidazole. The corresponding complexes exhibit the highest ascertained order of anti-tumor activity when compared against other complexes in this series and against known analogs.

It is essential for activity that the nitrogen atom of the imidazole nucleous be substituted by a lower alkyl moiety, a fact which can be demonstrated by comparing the %ILS values for trichloro(imidazole)gold(III) and trichloro(N-methylimidazole)gold(III) in Table 3. Thus, whereas, the former (Example 9) is inactive in bringing about a regression of S 180 ascites at all doses tested, the latter compound (Example 4) is decidedly active within the 20-40 mg/kg range.

PREPARATIVE METHOD

The products of this invention may be obtained by treating equimolar amounts of alkali metal tetrahaloaurate with the appropriate amine (L). The precipitate which forms is filtered from solution and it may be washed with water to afford a purified product:

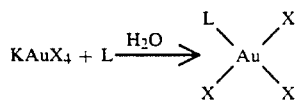

wherein Au represents gold in the trivalent state, L is an aliphatic amine, an aromatic amine or a heterocyclic amine of the type hereinbefore described and X is chloro or bromo. The reaction is preferably conducted with stirring at temperatures below about 25° C. and, most preferably, at temperatures of about 0° C.

This process is conducted in an aqueous solution such as water but other media as, for example, an alcohol such as methanol or ethanol also may be employed.

Certain of the products, for example, the [Au(nicotinic acid)$X_3$]and [Au(pyridylacetic acid)$X_3$]of Examples 1, 4, 10 and 11 are soluble in 1% sodium bicarbonate solution to the extent of 12.8 mg/ml.

The infrared spectral data shows intense AuCl bands at approximately 350 cm$^{-1}$ for all analyzed complexes and this is consistent with the assigned structure for the products.

Gold content was determined by the gravimetric method described by F. E. Beamish in "The Analytical Chemistry of the Noble Metals"; Pergamon Press, Oxford, page 321 (1966).

PHARMACOLOGY

The products of this invention are useful in the treatment of tumors in animals as, for example, Sarcoma 180 ascites tumors in mammals such as mice. This anti-tumor effect also may extend to other sarcomas and to such other tumors as the following: lymphoid leukemia, lymphosarcoma, myelocytic leukemia, malignant lymphoma, squamous cell carcinoma, adenocarcinoma, scirrhous carcinoma, malignant melanoma, seminoma, teratoma, choriocarcinoma, embryonalcarcinoma, cystadenocarcinoma, endometroidcarcinoma or neuroblastoma and the like. In addition, said complexes may be useful as anti-viral, anti-inflammatory, anti-bacterial and anti-parasitic agents.

They may be administered parenterally or orally in admixture with a non-toxic pharmacologically acceptable inert carrier or diluent in any of the usual pharmaceutical forms. These include solid and liquid oral unit dosage forms such as tablets, capsules, powders and suspensions or solutions and suspensions for subcutaneous, intramuscular, intravenous or intra-arterial injection.

The term "unit dosage" refers to physically discrete units which may be administered in single or multiple dosages each containing a predetermined quantity of the active ingredient in association with the required diluent, carrier or vehicle. The quantity of active ingredient is the amount of the complex which is needed to produce the desired therapeutic effect.

A typical unit dosage consists essentially of from about 5–250 mg. of active ingredient; however, the form in which said ingredient is administered and the frequency of administration is usually determinative of the concentration. Thus, for example, oral unit dosage forms containing 5–250 mg. of active ingredient may be administered one or more times per day depending upon the severity of the tumor which is sought to be treated and the condition of the host animal. By contrast, parenteral administration generally requires from about 10–125 mg. of the active ingredient per unit dosage administered as a daily dose or as a fraction thereof depending upon whether the regimen calls for administration once, twice, three or four times daily.

By contrast to the "unit dosage", the effective dose is that dosage which is needed to achieve the desired anti-tumor effect. In general, this dosage lies within the range of from about 2–480 mg. of the active ingredient per kg. of body weight of the host animal. A preferred concentration lies within the range of from about 5–250 mg./kg. of body weight. For oral administration it has been found that an effective dose of 8–480 mg./kg. is most suitable, whereas, in the case of parenteral administration it is usually advisable to employ from about 2–80 mg./kg. These dosages are well below the toxic or lethal dose and they may be varied over a wide range for adjustment to the patient which is being treated.

In this invention the term "pharmacologically acceptable inert carrier or diluent" denotes a non-toxic substance which, when mixed with the active ingredient, renders it more suitable for administration. Compositions intended for oral administration may include such carriers or diluents as corn starch, potato starch, sodium carboxymethyl cellulose, ethyl cellulose, cellulose acetate, powdered gum tragacanth, gelatin, alginic acid, agar, stearic acid or the sodium, calcium and magnesium salts of stearic acid, sodium lauryl sulfate, polyvinylpyrrolidone, sodium citrate, calcium carbonate and dicalcium phosphate. Said compositions may also contain non-toxic adjuvants and modifiers such as dyes, buffering agents, preservatives, surfactants, emulsifiers, flavoring agents or biocides and the like.

Tablets are prepared by mixing a complex of this invention in a suitably comminuted or powdered form with a diluent or base such as starch, kaolin, dicalcium phosphate and the like. The resulting mixture can be granulated by wetting with a binder such as a syrup, starch (paste), acacia mucilage or solutions of cellulosic or polymeric materials, whereafter, the wetted mixture is forced through a screen. As an alternative to granulating, the powdered mixture can be run through a tablet machine and imperfectly formed slugs broken into granules. The granules are lubricated to prevent sticking to the tablet-forming dies via the addition of stearic acid, a stearate salt, talc or mineral oil and the lubricated mixture is then compressed into tablets. The complexes can also be combined with free flowing inert carriers followed by compression into tablets without going through the granulating or slugging steps. A protective coating or sealing coat of shellac, sugar or polymeric material and a polished coating of wax can also be provided. Dyestuffs may be added to distinguish different unit dosages.

Capsules are formulated by preparing a powdered mixture, according to the procedure hereinbefore described and pouring said mixture into preformed gelatin sheaths. A lubricant such as talc, magnesium stearate or calcium stearate can be added as an adjuvant prior to the filling operation. A glidant such as colloidal silica may be added to improve the flow characteristics and a disintegrating or solubilizing agent may also be added to enhance the effectiveness of the medicament upon ingestion.

Powders are prepared by comminuting the compound to a fine size and mixing with a similarly comminuted pharmaceutical diluent or carrier such as an edible carbohydrate as, for example, starch. Sweetening agents and flavorings, preservatives and dispersing and/or coloring agents may also be employed.

Oral fluids such as syrups and elixirs are prepared in unit dosage form so that a given quantity of medicament, such as a teaspoonful, will contain a predetermined amount of the active ingredient. Suspensions can be formulated by dispersing the active ingredient in a non-toxic vehicle in which it is essentially insoluble.

Fluid unit dosage forms for parenteral administration can be prepared by placing a measured amount of the complex in an ampoule or vial which is sterilized and sealed. An accompanying vial or vehicle can be provided for mixing with said complex prior to administration.

This invention also provides for combining two or more of the subject complexes into a single unit dosage form or, alternatively, combining one or more of said complexes with other known anti-tumor agents, therapeutic agents or nutritive agents and the like so as to enhance or complement the antitumor effect.

The preferred compositions for oral administration are tablets in which the gold complex is present in quantities of 5–250 mg. but, preferably, 20–100 mg. in a pharmaceutically acceptable orally ingestible solid carrier. If desired, the composition may also contain flavors, binders, lubricants and other excipients known in the art.

A preferred alternative for oral administration is the soft gelatin capsule. Such a composition may contain from 5–250 mg. but, preferably, 20–100 mg. by weight of active ingredient dissolved or suspended in vegetable oil, peanut oil, alcohol or glycerine and the like.

The following embodiments illustrate representative unit dosage forms.

| Compressed Tablet | |
|---|---|
| A tablet suitable for swallowing is prepared by mixing the following ingredients: | |
| Trichloro(Nicotinic Acid)gold(III) | 50 mg. |
| Niacinamide | 50 mg. |
| Calcium Pantothenate | 20 mg. |
| Magnesium Sulfate | 50 mg. |
| Zinc Sulfate | 50 mg. |
| Magnesium Stearate | 10 mg. |

| Compressed Tablet | |
|---|---|
| | 230 mg. |

The trichloro(nicotinic acid)gold(III), niacinamide, calcium pantothenate, magnesium sulfate, zinc sulfate and magnesium stearate (5.0 mg.) are mixed and compressed into slugs. The slugs are then broken into granules and sifted through an 8 mesh screen. Additional magnesium stearate (5.0 mg.) is added and the mixture is then compressed into tablets suitable for oral administration.

| Soft Gelatin Capsule | |
|---|---|
| A soft elastic gelatin capsule is filled with the following ingredients: | |
| Trichloro(3-Acetylpyridine)gold(III) | 100 mg. |
| Wheat germ oil | 50 mg. |
| Sunflower seed oil | 100 mg. |
| | 250 mg. |

The trichloro(3-acetylpyridine)gold(III) and wheat germ oil are mixed with sunflower seed oil and the resulting mixture is poured into gelatin capsules suitable for oral administration. An alternative embodiment provides for substituting sunflower seed oil and wheat germ oil with equal amounts of peanut oil to obtain an otherwise similar capsule which is also suitable for oral administration.

| Dry Filled Capsule | |
|---|---|
| A hard dry-filled capsule may be prepared from the following ingredients: | |
| Trichloro(Nicotinic Acid)gold(III) | 75 mg. |
| Niacinamide | 50 mg. |
| Calcium Pantothenate | 10 mg. |
| | 135 mg. |

The trichloro(nicotinic acid)gold(III) is reduced to a No. 60 powder. Niacinamide and calcium pantothenate are passed through a No. 60 bolting cloth and the ingredients are added to the trichloro(nicotinic acid)gold(III). This combination of ingredients is mixed for 10 minutes and then poured into a No. 3 size gelatin capsule.

Dry Powder

The following composition illustrates a representative dosage in dry powder form. In this embodiment the active ingredient is combined with up to 60% by weight of a suitable flavoring agent. All quantities are in a weight-percent relationship.

| Trichloro(N-Methylimidazole)gold(III) | 25–90% |
|---|---|
| Flavoring Agent | 10–60% |
| Preservative | 0–1.0% |

The trichloro(N-methylimidazole)gold(III), flavoring agent and preservative are thoroughly blended to afford a homogeneous dry powder. The resulting formulation may be blended with other therapeutic agents to afford combination-type medicinals. Alternatively, said powder may be dissolved in a pharmacologically acceptable diluent to afford a solution which is suitable for oral administration.

Compositions intended for parenteral administration may include such diluents and carriers as water-miscible solvents as, for example, sesame oil, ground nut oil and aqueous propylene glycol. Typical of said compositions are solutions which contain the active ingredient in sterile form. An embodiment illustrating a dosage form suitable for intravenous injection is set forth below.

Parenteral Solution

Injectable solutions can be formulated by mixing an ampoule of active ingredient with an ampoule of sterile diluent:

| Ampoule: | Trichloro(Nicotinic Acid)gold(III) | 100 mg. |
|---|---|---|
| Ampoule: | Sterile 1% NaHCO$_3$ (Diluent for Injection) | 10 cc. |

The trichloro(nicotinic acid)gold(III) and aqueous NaHCO$_5$ are mixed thoroughly immediately prior to administration. If desired, one or more other active ingredients may be added to provide an injectable solution having enhanced therapeutic activity.

The following embodiments illustrate the methods by which the products (I) of this invention are obtained, however, it is to be understood that said embodiments are merely illustrative and they are not to be construed as being limitative of the invention herein described and claimed.

Example 1

Trichloro(Nicotinic Acid)Gold(III)

Potassium tetrachloroaurate (KAuCl$_4$ 2H$_2$O; 1.04 g, 2.5 mmoles) was dissolved in water (10 ml) and the solution cooled to 0° C. A suspension of nicotinic acid (0.308g, 2.5 mmoles) in water (5 ml) was added and the mixture was stirred at 0° C. for 10 minutes. The resulting yellow product was filtered, washd with two 10 ml portions of water and vacuum dried to afford 0.79g (74.1%) of trichloro(nicotinic acid)gold(III).

Gold Analysis for AuC$_6$H$_5$NO$_2$Cl$_3$.2H$_2$O: Calculated: 42.59%, Found: 42.47%.

EXAMPLE 2

Trichloro(N-Methylimidazole)Gold(III)

The procedure of Example 1 was repeated except that an equmolar quantity of N-methylimidazole was substituted for the nicotinic acid therein described. The resulting trichloro(N-methylimidazole)gold(III) afforded the following analysis:

Analysis for AuC$_4$H$_6$N$_2$Cl$_3$.H$_2$O

| | % Au | % C | % H | % N |
|---|---|---|---|---|
| Calculated: | 48.82 | 12.46 | 1.57 | 7.27 |
| Found: | 49.21 | 12.20 | 1.53 | 7.15 |

The procedure of Example 1 also was used to produce a variety of other trivalent gold complexes. The following equation and Table illustrate this procedure, the starting materials employed and the products obtained thereby:

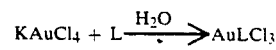

TABLE 1

| | | AuLCl₃ Complexes | | |
| | | Empirical | Au Analysis (%) | |
| Ex. | L | Formula | *Calculated | Found |
|---|---|---|---|---|
| 3 | 3-Acetylpyridine | $AuC_7H_7NOCl_3$ | 46.40 | 45.58 |
| 4 | 3-Pyridylacetic Acid | $AuC_7H_7NO_2Cl_3(4H_2O)$ | 38.43 | 38.37 |
| 5 | 3-Hydroxypyridine | $AuC_5H_5NOCl_3(4H_2O)$ | 41.86 | 41.97 |
| 6 | 3-Pyridylcarbinol | $AuC_6H_7NOCl_3(1H_2O)$ | 45.75 | 46.69 |
| 7 | **Pyridine | $AuC_5H_5NCl_3(1H_2O)$ | 49.19 | 49.84 |
| 8 | Imidazole | $AuC_3H_4N_2Cl_3$ | 53.03 | 52.93 |

*The water of hydration is assumed.
**This product, trichloro(pyridine)gold(III), is referred to by L. Cattalini et al in "Inorganic Chemistry", Vol. 5: pages 1145–1150 (1966), though no utility is suggested for it.

EXAMPLE 9

Tribromo(N-Methylimidazole)Gold(III) ·

By repeating the procedure of Example 1 but substituting potassium tetrabromoaurate and N-methylimidazole for the potassium tetrachloroarate and nicotinic acid therein described there was thus obtained tribromo(N-methylimidazoles)gold(III) in crystalline form.

Gold Analysis for $AuC_4H_6N_2Br_3 \cdot 1H_2O$ Calculated: 36.69%, Found: 36.54%.

The procedure of example 9 also was used to produce a variety of trivalent gold complexes. The following equation and Table illustrate this procedure, the starting materials employed and the products obtained thereby:

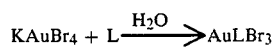

$$KAuBr_4 + L \xrightarrow{H_2O} AuLBr_3$$

TABLE 2

| | AuLBr₃ Complexes |
| Ex. | L |
|---|---|
| 10 | Nicotinic Acid |
| 11 | 3-Pyridylacetic Acid |

By following the procedure of Examples 1 and 9 various other $AuLX_3$ complexes are obtained. The following equation and Table illustrate this method, the starting materials employed and the gold(III) complexes which may be obtained thereby:

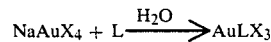

$$NaAuX_4 + L \xrightarrow{H_2O} AuLX_3$$

TABLE 3

| | AuLX₃ Complexes | |
| Example | L | X |
|---|---|---|
| 12 | Methylamine | Cl |
| 13 | Pyrazine | Br |
| 14 | 3-Methoxypyridine | Cl |
| 15 | Pyrazole | Cl |
| 16 | Pyrimidine | Cl |
| 17 | tert.-Butylamine | Br |
| 18 | Ammonia (NH₃) | Cl |
| 19 | Pyridazine | Cl |
| 20 | 3-Methylpyrazine | Br |
| 21 | 5-acetylpyrimidine | Cl |
| 22 | Quinoline | Cl |
| 23 | Quinoline | Br |
| 24 | Isoquinoline | Br |
| 25 | NH₃ | Cl |

The products of Examples 22–24 are described by Cattalini et al in the "Inorganic Chemistry" publication cited above. The product of example 25 is cited by J. Straehle, J. Gelinek, and M. Koelmel in Z. Anorg. Allg. Chem., Vol 456: pages 241–260 (1979). There is, however, no disclosure in either publication relative to the use of said products as anti-tumor agents. Accordingly, these products share with the novel products of this invention a common utility and, taken together, they form the basis for the method of treatment claims which have been appended to this Specification. In said claims the ligands which embrace ammonia, quinoline and isoquinoline are identified as "$L^2$".

ANTI-TUMOR EVALUATION

The above prepared compounds were evaluated against S180 ascites in female CFW Swiss mice. The mice were weighed (average weight: 20 g), placed into cages (six mice to a cage) and on day zero the mice were inoculated with 0.2 ml of a freshly prepared saline suspension (0.15 M NaCl) containing $1 \times 10^7$ tumor cells/ml or a total of $2 \times 10^6$ cells. This inoculum was freshly prepared using "transfer" mice which had been injected with tumor cells the previous week; it was obtained via the following steps: (1) the removal of cells from the peritoneal cavity of the sacrificed transfer mouse, (2) alternate centrifugation and washing operations (2–3 times with cold saline) to remove blood and other components, and (3) dilution of the volume of the packed cell with saline (1:3). A final centrifugation was carried out at 1000 RPM over a two minute period. A cell count was made on a 2,000-fold dilution of this 1:3 suspension by means of a Coulter Counter. A final dilution to $1 \times 10^7$ cells/ml was made based on the average count.

On day 1, solutions of the test compounds were prepared and each mouse in a set of six were injected with the same test compound at the same dosage. The doses were based on the average weight of the animals (cage weight). Also, beginning on day 1 two controls were employed containing six mice per control:

(1) Normal Control: This consisted solely of the carrier or diluent used in combination with the test compound; and (2) Positive Control: This consisted solely of the known anti-tumor agent cis-$[Pt(NH_3)_2Cl_2]$ (Cisplatin) in saline (8 mg/kg) to test the response of the biological system.

The effectiveness of a test compound was measured in terms of the % increase in life span (%ILS) of the test mice relative to the Normal Control (Calculated from the day of tumor inoculation, i.e., day zero). To standardize the test data and permit intercomparisons, the day of evaluation was arbitrarily taken as that day corresponding to twice the mean life span (or average day of death) of the control. This established a practical upper limit of 100% on the %ILS attainable. For calculation purposes the survivors on the day of evaluation were considered to have died on that day. The %ILS was calculated as follows:

$$\%ILS = \left( \frac{\text{mean-life span of test mice}}{\text{mean-life span of control mice}} - 1 \right) \times 100\%$$

ILS values in excess of 50% were interpreted as being indicative of anti-tumor activity, whereas, values in excess of 75% indicated excellent activity.

The products of Examples 1, 4, 10 and 11 were administered in a freshly prepared 1% sodium bicarbonate solution; the remaining test compounds were administered as slurries in 0.5% "Klucel" (hydroxypropylcellulose). All products (I) are insoluble in water. The results of this study are summarized in Table 4.

TABLE 4

Anti-Tumor Screening Data: S 180 Ascites

| Example; (Compound) | Dose (mg/kg) | % ILS | Survivors | Positive Control % ILS | Survivors |
|---|---|---|---|---|---|
| Ex. 1 | | | | | |
| Au(Nicotinic-acid)Cl₃ | 10 | −3 | 0 of 6 | 60 | 0 of 6 |
| | 20 | 60 | 3 of 6 | | |
| | 40 | 91 | 3 of 6 | | |
| | 80 | 98 | 4 of 6 | | |
| | 160 | 1 | 0 of 6 | | |
| | 320 | −69 | 0 of 6 | | |
| Ex. 2 | | | | | |
| Au(N-Methylimidazole)Cl₃ | 5 | 2 | 0 of 6 | 49 | 0 of 6 |
| | 10 | 14 | 0 of 6 | | |
| | 20 | 33 | 1 of 6 | | |
| | 40 | 91 | 4 of 6 | | |
| | 80 | 53 | 1 of 6 | | |
| | 160 | −93 | 0 of 6 | | |
| Ex. 3 | | | | | |
| Au(3-Acetylpyridine)Cl₃ | 10 | −5 | 0 of 6 | 52 | 0 of 6 |
| | 20 | 42 | 1 of 6 | | |
| | 40 | 97 | 5 of 6 | | |
| | 80 | 66 | 4 of 6 | | |
| | 160 | 23 | 0 of 6 | | |
| | 320 | −90 | 0 of 6 | | |
| Ex. 4 | | | | | |
| Au(3-Pyridylacetic Acid)Cl₃ | 10 | 6 | 0 of 6 | 60 | 0 of 6 |
| | 20 | −15 | 0 of 6 | | |
| | 40 | 63 | 1 of 6 | | |
| | 80 | 57 | 1 of 6 | | |
| | 160 | −41 | 0 of 6 | | |
| | 320 | −90 | 0 of 6 | | |
| Ex. 5 | | | | | |
| Au(3-Hydroxypyridine)Cl₃ | 10 | 9 | 0 of 6 | 96 | 4 of 6 |
| | 20 | 39 | 2 of 6 | | |
| | 40 | 61 | 3 of 6 | | |
| | 80 | 30 | 2 of 6 | | |
| | 160 | −36 | 0 of 6 | | |
| | 320 | −85 | 0 of 6 | | |
| Ex. 6 | | | | | |
| Au(3-Pyridylcarbinol)Cl₃ | 10 | 6 | 0 of 6 | 96 | 4 of 6 |
| | 20 | 63 | 1 of 6 | | |
| | 40 | 85 | 3 of 6 | | |
| | 80 | 46 | 0 of 6 | | |
| | 160 | −70 | 0 of 6 | | |
| | 320 | −93 | 0 of 6 | | |
| Ex. 7 | | | | | |
| Au(Pyridine)Cl₃ | 10 | 45 | 3 of 6 | 100 | 6 of 6 |
| | 20 | 71 | 2 of 6 | | |
| | 40 | 66 | 3 of 6 | | |
| | 80 | −6 | 2 of 6 | | |
| | 160 | −94 | 0 of 6 | | |
| | 320 | −94 | 0 of 6 | | |

TABLE 4-continued

Anti-Tumor Screening Data: S 180 Ascites

| Example; (Compound) | Dose (mg/kg) | % ILS | Survivors | Positive Control % ILS | Survivors |
|---|---|---|---|---|---|
| Ex. 8 | | | | | |
| Au(Imidazole)Cl₃ | 5 | 5 | 0 of 6 | 49 | 0 of 6 |
| | 10 | −7 | 0 of 6 | | |
| | 20 | 1 | 1 of 6 | | |
| | 40 | −16 | 0 of 6 | | |
| | 80 | 37 | 1 of 6 | | |
| | 160 | 37 | 2 of 6 | | |
| Ex. 9 | | | | | |
| Au(N-Methylimidazole)Br₃ | 10 | 5 | 0 of 6 | 52 | 0 of 6 |
| | 20 | 76 | 4 of 6 | | |
| | 40 | 66 | 3 of 6 | | |
| | 80 | −1 | 1 of 6 | | |
| | 160 | −94 | 0 of 6 | | |
| | 320 | −94 | 0 of 6 | | |
| Ex. 10 | | | | | |
| Au(Nicotinic Acid)Br₃ | 10 | −23 | 0 of 6 | 40 | 1 of 6 |
| | 20 | 26 | 0 of 6 | | |
| | 40 | 64 | 2 of 6 | | |
| | 80 | 49 | 0 of 6 | | |
| | 160 | −19 | 0 of 6 | | |
| | 320 | −95 | 0 of 6 | | |
| Ex. 11 | | | | | |
| Au(3-Pyridylacetic Acid)Br₃ | 10 | −16 | 0 of 6 | 40 | 1 of 6 |
| | 20 | 20 | 0 of 6 | | |
| | 40 | 10 | 0 of 6 | | |
| | 80 | 31 | 1 of 6 | | |
| | 160 | −21 | 0 of 6 | | |
| | 320 | −92 | 0 of 6 | | |

Peak activity was observed at 20-80 mg/kg for all of the test compounds and toxicity occurred within the range of 160-320 mg/kg. The following three compounds exhibited peak ILS values in excess of 90%: trichloro(nicotinic acid)gold(III), [Example 1], trichloro(N-methylimidazole)gold(III) and trichloro(3-acetylpyridine)gold(III).

The trichloro(imidazole)gold(III) of Example 8 and the tribromo(3-pyridylacetic acid)gold(III) of Example 11 failed to meet the 50% ILS criterion for anti-tumor activity and, therefore, they are considered to be inactive in this study.

The therapeutic indices for the present compounds (I), their effective dose (ED₉₀) and lethal dose (LD₅₀) were determined according to the method of Miller and Tainter (Reported by R. A. Turner, "Screening Methods in Pharmacology", Academic Press, New York, pages 61-62 (1976)). This study was conducted with implanted Sarcoma 180 tumors in Swiss white mice and the results of this study are set forth in Table 5; ED90 represents the dose which resulted in a 50% increase in life span (ILS) for 90% of the animals tested, determined graphically, and LD₅₀ represents the lethal dose to 50% of said animals (Therapeutic index: LD₅₀/ED₉₀).

TABLE 5

Therapeutic Indices: S 180 Ascites

| Example (Compound) | Maximum % ILS (Dosage) | ED₉₀ | LD₅₀ | Therapeutic Index |
|---|---|---|---|---|
| Ex. 1 | | | | |
| Au(Nicotinic Acid)Cl₃ | 98(80 mg/kg) | 31 | 180 | 5.8 |
| Ex. 2 | | | | |
| Au(N-Methylimidazole)Cl₃ | 91(40 mg/kg) | 31 | 90 | 2.8 |
| Ex. 3 | | | | |

TABLE 5-continued

Therapeutic Indices: S 180 Ascites

| Example (Compound) | Maximum % ILS (Dosage) | ED$_{90}$ | LD$_{50}$ | Therapeutic Index |
|---|---|---|---|---|
| Au(3-Acetyl-pyridine)Cl$_3$ Ex. 4 | 97(40 mg/kg) | 31 | 140 | 4.5 |
| Au(3-Pyridyl-acetic Acid)Cl$_3$ Ex. 5 | 63(40 mg/kg) | 84 | 150 | 1.8 |
| Au(3-Hydroxy-pyridine)Cl$_3$ Ex. 6 | 61(40 mg/kg) | 87 | 120 | 1.4 |
| Au(3-Pyridyl-carbinol)Cl$_3$ *Ex. 7 | 85(40 mg/kg) | 43 | 90 | 2.1 |
| Au(Pyridine)Cl$_3$ Ex. 9 | 71(20 mg/kg) | 35 | 80 | 2.3 |
| Au(N-Methylimi-dazole)Br$_3$ | 76(20 mg/kg) | 42 | 85 | 2.0 |

*This product is described by Cattalini et al in the publication entitled "Inorganic Chemistry" cited above.

All of the test compounds exhibited indices which exceed the 1.0 threshold limit. The trichloro(nicotinic acid)gold(III) of Example 1 and the trichloro(3-acetylpyridine)gold(III) of Example 3 afforded indices of 5.8 and 4.5 respectively, figures which compare favorably with the 2.2-2.5 value attributed to commercially available Cisplatin.

On the basis of the following the complexes of this invention have been determined to be effective antitumor agents; however, the products herein-described are merely illustrative of the invention and it is to be understood that alterations in structure are within the skill of the artisan to effect. Accordingly, any derivatives of the herein-described compounds which prove useful in the treatment of tumors are to be considered as being within the scope of this invention.

What is claimed is:

1. A compound having the formula:

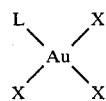

wherein Au is gold in its trivalent state; L is a substituted pyridine of the formula:

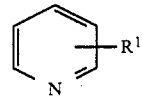

wherein $R^1$ is selected from the group consisting of $C_{1-6}$ alkyl, carboxy, $C_{2-6}$ alkanoyl, $-C_nH_{2n}COOH$ wherein n is 1 to 6, hydroxy, carbinol and $C_{1-6}$ alkoxy; and wherein X is chlorine or bromine with the proviso that when L represents 3-pyridylacetic acid X is chlorine.

2. A compound according to claim 1, wherein $R^1$ is carboxy.

3. A compound according to claim 1, wherein $R^1$ is $-C_nH_{2n}COOH$ wherein n=1 to 6.

4. A compound according to claim 1, wherein $R^1$ is carbinol.

5. A compound according to claim 1, wherein $R^1$ is hydroxy.

6. A compound according to claim 1, wherein $R^1$ is $C_{1-6}$ alkyl.

7. A compound according to claim 1, wherein $R^1$ is $C_{2-6}$ alkanoyl.

8. A compound according to claim 1, wherein $R^1$ is $C_{1-6}$ alkoxy.

9. A compound according to claim 1, wherein L is nicotinic acid.

10. A pharmaceutical composition comprising a compound of the formula:

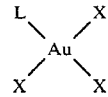

wherein Au represents gold in its trivalent state; L is a pyridine of the formula:

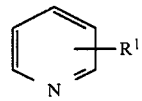

wherein $R^1$ is selected from the group consisting of hydrogen, $C_{1-6}$ alkyl, carboxy, $C_{2-6}$ alkanoyl, carbinol, $-C_nH_{2n}COOH$ wherein n is 1 to 6, hydroxy, and $C_{1-6}$ alkoxy; and wherein X is chlorine or bromine, with the proviso that when L represents 3-pyridylacetic acid, X is chlorine; in combination with a non-toxic pharmaceutically acceptable inert carrier or diluent.

11. A composition according to claim 10, wherein $R^1$ is carboxy.

12. A composition according to claim 10, wherein $R^1$ is $C_{1-6}$ alkyl.

13. A composition according to claim 10, wherein $R^1$ is $C_{1-6}$ alkoxy.

* * * * *